(12) United States Patent
Hartley

(10) Patent No.: US 10,231,822 B2
(45) Date of Patent: Mar. 19, 2019

(54) THORACIC AORTA STENT GRAFT

(71) Applicant: Cook Medical Technologies LLC, Bloomington, IN (US)

(72) Inventor: David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 116 days.

(21) Appl. No.: 15/593,715

(22) Filed: May 12, 2017

(65) Prior Publication Data
US 2017/0245978 A1    Aug. 31, 2017

Related U.S. Application Data

(63) Continuation of application No. 13/576,348, filed as application No. PCT/US2011/024148 on Feb. 9, 2011, now Pat. No. 9,649,188.
(Continued)

(51) Int. Cl.
*A61F 2/07* (2013.01)
*A61F 2/915* (2013.01)
(Continued)

(52) U.S. Cl.
CPC .............. *A61F 2/07* (2013.01); *A61F 2/915* (2013.01); *A61F 2/856* (2013.01); *A61F 2/89* (2013.01);
(Continued)

(58) Field of Classification Search
CPC ...... A61F 2/07–2002/077; A61F 2/856; A61F 2/954; A61F 2002/826; A61F 2/852
See application file for complete search history.

(56) References Cited

U.S. PATENT DOCUMENTS 6,187,033 B1   2/2001   Schmitt et al.
6,645,242 B1   11/2003  Quinn
(Continued)

FOREIGN PATENT DOCUMENTS

AU   2010202544 B1   8/2010
JP   2005-521471     7/2005
(Continued)

OTHER PUBLICATIONS

Examination report for corresponding EP Application No. 11703804. 2-1651, dated Apr. 2, 2015, 6 pgs.
(Continued)

*Primary Examiner* — Yashita Sharma
*Assistant Examiner* — Rebecca Preston
(74) *Attorney, Agent, or Firm* — Brinks Gilson & Lione

(57) ABSTRACT

A stent graft for placement in the thoracic arch of a patient has a tubular body defining a main lumen therethrough, a plurality of zig zag stents along the tubular body, each of the stents comprising a plurality of struts and bends, the bends being between adjacent struts. At least a first stent and an adjacent second stent having at least a pair of adjacent bends on the first stent aligned with an adjacent pair of bends on the second stent, whereby a first pair of adjacent struts of the first stent and a second pair of adjacent struts of the second adjacent stent together define a diamond shape region. A recess is within the diamond shaped region with the recess extending into the lumen of the tubular body. A fenestration extending into the tubular body within the recess in the diamond shaped region and a graft tube leading from the fenestration into the main lumen. There can be one, two or three diamond shaped regions, recesses, fenestrations and graft tubes. Proximally of the or each diamond shaped region the tubular body has a first diameter, distally of the diamond shaped region the tubular body has a second
(Continued)

diameter and in the region of the tubular body around the diamond shaped region the tubular body has a third diameter, the first diameter being greater than the second diameter and both the first and second diameter being greater than the third diameter whereby a central region is defined which will allow circumferential blood flow during an operation out of the graft tube into the recess and then into the central region.

21 Claims, 5 Drawing Sheets

Related U.S. Application Data

(60) Provisional application No. 61/302,586, filed on Feb. 9, 2010.

(51) Int. Cl.
  A61F 2/856    (2013.01)
  A61F 2/954    (2013.01)
  A61F 2/82     (2013.01)
  A61F 2/06     (2013.01)
  A61F 2/89     (2013.01)

(52) U.S. Cl.
  CPC ......... *A61F 2/954* (2013.01); *A61F 2002/061* (2013.01); *A61F 2002/075* (2013.01); *A61F 2002/826* (2013.01); *A61F 2210/0014* (2013.01)

(56) References Cited

U.S. PATENT DOCUMENTS

| | | | |
|---|---|---|---|
| 6,723,116 | B2 | 4/2004 | Taheri |
| 7,537,606 | B2 | 5/2009 | Hartley et al. |
| 7,645,298 | B2 | 1/2010 | Hartley et al. |
| 2003/0199967 | A1 | 10/2003 | Hartley et al. |
| 2005/0102021 | A1 | 5/2005 | Osborne |
| 2005/0131517 | A1 | 6/2005 | Hartley et al. |
| 2006/0184228 | A1* | 8/2006 | Khoury ............. A61F 2/07 623/1.13 |
| 2008/0109066 | A1 | 5/2008 | Quinn |
| 2008/0281399 | A1 | 11/2008 | Hartley et al. |
| 2009/0125095 | A1 | 5/2009 | Bui et al. |
| 2009/0248135 | A1 | 10/2009 | Bruszewski et al. |
| 2009/0254170 | A1 | 10/2009 | Hartley |
| 2009/0306763 | A1 | 12/2009 | Roeder et al. |
| 2010/0063576 | A1 | 3/2010 | Schaeffer et al. |
| 2010/0069853 | A1 | 3/2010 | Zukowski |
| 2010/0268327 | A1 | 10/2010 | Bruszewski et al. |
| 2010/0312326 | A1 | 12/2010 | Chuter et al. |
| 2011/0054594 | A1 | 3/2011 | Mayberry et al. |
| 2011/0087319 | A1 | 4/2011 | Hagaman et al. |

FOREIGN PATENT DOCUMENTS

| | | |
|---|---|---|
| JP | 2012-501208 A | 1/2012 |
| WO | WO 2003/082153 A2 | 10/2003 |
| WO | WO 2008/021557 A1 | 2/2008 |
| WO | WO 2010/024879 A1 | 3/2010 |
| WO | WO 2011/159324 A1 | 12/2011 |

OTHER PUBLICATIONS

First Examination Report for Australian Patent Application No. 2011215968 dated Jan. 24, 2013, 2 pgs.
Japanese Office Action/Notification for Reason for Rejection for corresponding JP 2012-552939, dated Dec. 2, 2014, 4 pgs.
Japanese Office Action and English translation for JP Patent Application No. 2012-552939, dated Sep. 8, 2015, 4 pgs.
Notification of Transmittal of the International Search Report and the Written Opinion of the International Searching Authority, International Application No. PCT/US2011/024148, dated Apr. 12, 2011, p. 1-13.
International Preliminary Report on Patentability for PCT/US2011/024148, dated Aug. 14, 2012, 8 pgs.
Canadian Office Action for CA Application No. 2,788,838, dated Jun. 29, 2016, 2 pgs.

\* cited by examiner

THORACIC AORTA STENT GRAFT

RELATED APPLICATIONS

This application is a continuation of U.S. Ser. No. 13/576,348, filed Jul. 31, 2012, which is a National Stage of International Application No. PCT/US2011/024148, filed Feb. 9, 2011, which claims the benefit of the filing date under 35 U.S.C. § 119(e) of Provisional U.S. Patent Application Ser. No. 61/302,586, filed Feb. 9, 2010. All of the foregoing applications are hereby incorporated by reference in their entirety.

BACKGROUND

1. Technical Field

This invention relates to a medical device for treatment of aortic arch disease and more particularly to a stent graft for deployment into the thoracic aorta of a patient for that purpose.

2. Background Information

In recent years endovascular implantable devices have been developed for treatment of aortic aneurysms. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system whereafter the delivery system is inserted into the vascular system of the patient such as through a femoral incision. The leading end of the delivery system is maneuvered to the treatment site over a previously positioned guide wire. Through manipulation of a control system that extends to the proximal end of the catheter from the distal end of the system outside the patient the implantable device is then deployed by holding the device at its location and withdrawing a surrounding sheath. The stent graft or implantable device can then self expand or is expanded through the use of a balloon which is introduced with the stent graft introduction device. The stent graft becomes anchored into position to healthy wall tissue in the aorta such as by barbs whereafter the delivery system is then removed leaving the device in position to reverse an aneurysm in the aorta in a manner that channels all blood flow through the stent graft so that no blood flow enters the aneurysm thereafter, such that not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian and for treatment of an aneurysm in the region of the thoracic arch provision must be made for blood supply to continue to these arteries. For this purpose fenestrations are provided into the wall of a stent graft in that region. Access is generally obtained to these fenestrations, to deploy side arms into the stent graft, via the left or right brachial arteries or less commonly via the left or right carotid arteries. Once into the thoracic arch via such an artery the fenestration in the stent graft must be catheterised.

If a stent graft has been deployed into the thoracic aorta around the arch such that its fenestrations are not aligned precisely with their corresponding great vessels of the arch, then it can be difficult to access the fenestrations through corresponding vessels (such as the brachiocephalic and the left brachial arteries).

It is the object of this invention to provide an arrangement of stent graft to overcome the above problem or to at least provide the practitioner with a useful alternative.

Throughout this specification the term distal with respect to a portion of the aorta, a deployment device or a prosthesis such as a stent graft is intended to mean the end of the aorta, deployment device or prosthesis such as a stent graft further away in the direction of blood flow from the heart and the term proximal is intended to mean the portion of the aorta, deployment device or end of the prosthesis nearer to the heart. For other lumens within the human or animal body the terms caudal and cranial respectively should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

BRIEF SUMMARY

In one form therefore the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and bends, the bends being between adjacent struts;

at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;

a recess in the diamond shaped region, the recess being defined by a concave portion of graft material and the recess extending into the lumen of the tubular body, the recess having a proximal end;

a fenestration in the concave portion of graft material, the fenestration opening into the tubular body within the recess in the diamond shaped region; and a graft tube leading from the fenestration into the main lumen.

Preferably the fenestration and graft tube extend from the proximal end of the recess.

In one form the stent graft further comprises:

a third adjacent stent, the third adjacent stent having at least a pair of bends adjacent to the second stent whereby a third pair of adjacent stents of the third strut defines a second diamond shaped region, wherein the second diamond shaped region shares a strut with the first diamond shaped region.

Preferably the stent graft comprises one, two or three diamond shaped regions, each diamond shaped region comprising a respective recess, fenestration and graft tube.

Preferably the stent graft comprises a proximal end and a distal end and the, or each, graft tube extends within the main lumen towards the proximal end of the stent graft.

Preferably the bends and adjacent struts define an included angle in the range of from 40 to 80 degrees.

Preferably proximally of the diamond shaped region the tubular body has a first diameter, distally of the diamond shaped region the tubular body has a second diameter and in a region of the tubular body around the diamond shaped region the tubular body has a third diameter, the first diameter being greater than the second diameter and both the first and second diameter being greater than the third diameter whereby a central region is defined which will allow at least part circumferential blood flow during an operation out of the graft tube into the recess and then into the central region.

It will be seen that by this invention there is provided a stent graft for placement in the thoracic arch of a patient. The stent graft can be placed such that the intermediate portion is just proximal of the brachiocephalic artery and on the outside of the curve of the thoracic arch. By this placement there is defined, by the difference in diameter of the first and second portions, an open region outside the stent graft distal of the aperture in the step portion, so that blood flow can occur through the aperture to the open region enabling circulation to be preserved to the major vessels through the internal branches during the progress of an operation. As the intermediate portion is of stent graft is of a lesser diameter there is provided a working space in the recess in which a guide wire from the branch arteries can be directed to enter the internal tube to enable catheterisation. Subsequently a side branch stent graft can be deployed from the respective branch artery into the tube to provide blood flow into that branch artery.

In a preferred embodiment the first diameter can be from 35 to 50 mm, the second diameter can be from 40 to 30 mm, the third diameter can be from 20 to 40 mm. For instance in one embodiment the first diameter is 46 mm and the second and third diameters are 38 mm. In another embodiment the first and third diameters are 36 mm and the third diameter is 24 mm.

In one form the stents are formed from nitinol.

In one form the or each graft tube comprises a reinforcement in the form of a space frame.

In one form the space frame comprises a cylindrical portion the cylindrical portion comprising first and second circular ring portions spaced apart axially and at least two struts extending between the first and second circular ring portions and the graft tube being around the space frame.

In one form the cylindrical portion comprises an assembly of two individual ring and strut components, each ring and strut component comprising a circular ring portion defining a plane of the circular ring portion and a strut extending at right angles to the plane of the circular ring portion from a periphery of the circular ring portion.

In an alternative form the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and points or bends, the points or bends being between adjacent struts;

a shaped recess in the tubular body having a perimeter, the perimeter being formed at least in part at two adjacent struts of a first stent and two adjacent struts of a second adjacent stent;

the shaped recess being defined by a concave portion of graft material and the shaped recess extending into the lumen of the tubular body, the shaped recess having a proximal end;

a fenestration in the concave portion of graft material, the fenestration opening into the tubular body within the shaped recess; and a graft tube leading from the fenestration into the main lumen.

Preferably the fenestration and graft tube extend from the proximal end of the shaped recess.

In one form the stent graft further comprises:

a second shaped recess in the tubular body defined by a second perimeter, the second perimeter being formed at least in part at two adjacent struts of the second stent and two adjacent struts of a third adjacent stent.

In one form the stent graft further comprises: a proximal end and a distal end and the or each graft tube extends within the main lumen towards the proximal end of the stent graft.

Preferably the bends and adjacent struts define an included angle in the range of from 40 to 80 degrees.

In one form the stents are formed from nitinol.

In one form the or each graft tube comprises a reinforcement in the form of a space frame.

In one form the space frame comprises a cylindrical portion the cylindrical portion comprising first and second circular ring portions spaced apart axially and at least two struts extending between the first and second circular ring portions and the graft tube being around the space frame.

In one form the cylindrical portion comprises an assembly of two individual ring and strut components, each ring and strut component comprising a circular ring portion defining a plane of the circular ring portion and a strut extending at right angles to the plane of the circular ring portion from a periphery of the circular ring portion.

In a further alternative form the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and bends, the bends being between adjacent struts;

at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;

a recess in the diamond shaped region, the recess being defined by a concave portion of graft material and the recess extending into the lumen of the tubular body, the recess having a proximal end;

a fenestration in the concave portion of graft material, the fenestration opening into the tubular body within the recess in the diamond shaped region; and a graft tube leading from the fenestration into the main lumen, the fenestration and graft tube extending from the proximal end of the recess towards the proximal end of the stent graft.

BRIEF DESCRIPTION OF THE DRAWINGS

This then generally describes the invention but to assist with understanding reference will now be made to the accompanying drawings which show preferred embodiments of the invention.

In the drawings.

DETAILED DESCRIPTION OF THE DRAWINGS AND THE PRESENTLY PREFERRED EMBODIMENTS

Figure 5:
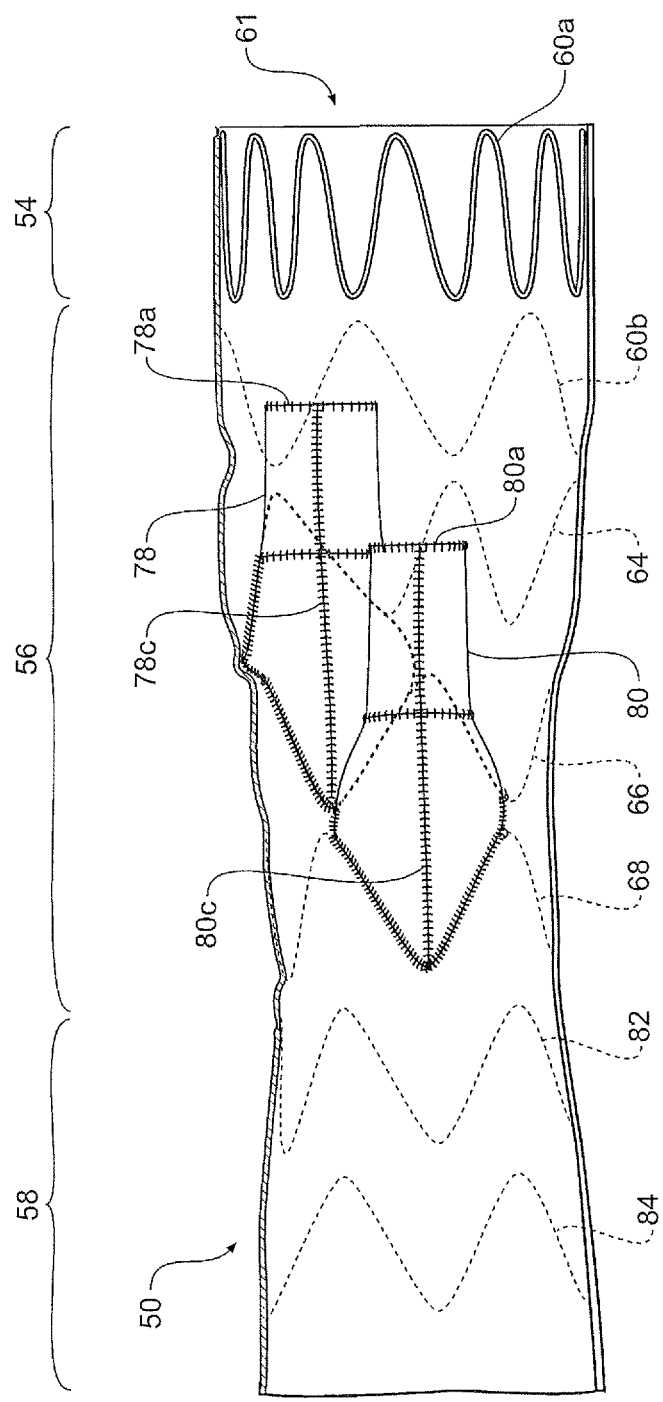
FIG. 5 shows a longitudinal cross-sectional view of the stent graft shown in FIG. 1.

FIGS. 1 to 6 show an embodiment of stent graft according to the present invention. In this embodiment the tubular body 52 of this embodiment of stent graft 50 comprises a proximal portion 54, an intermediate portion 56 and a distal portion 58 as shown in FIG. 5.

Figure 1:
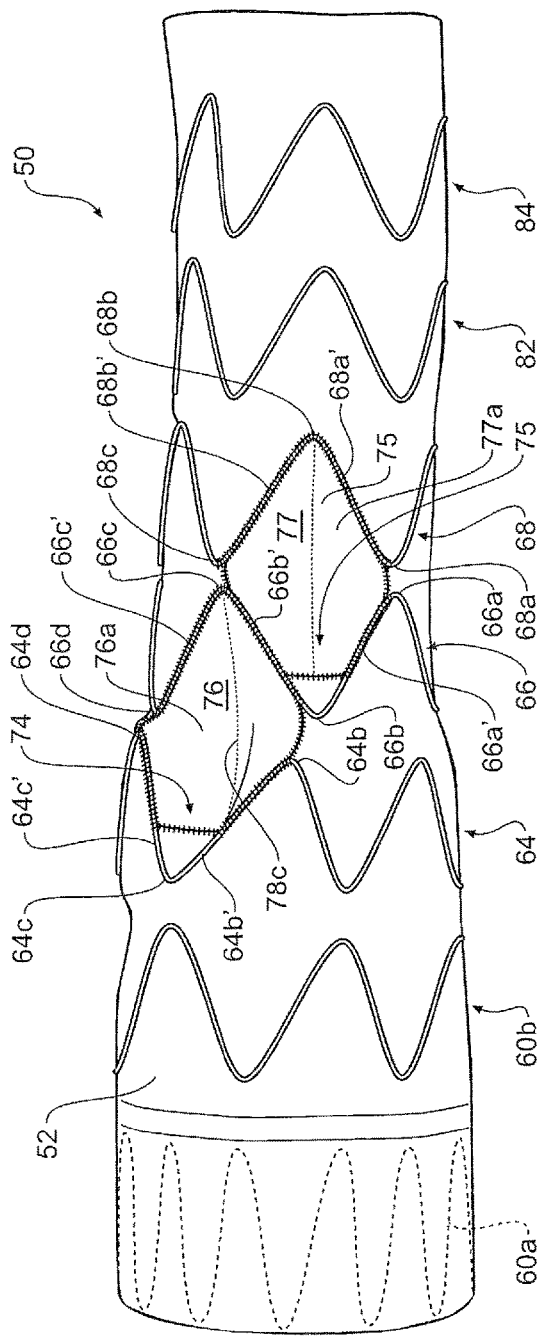
FIG. 1 shows a plain view of a first embodiment of a stent graft according to the present invention.
Figure 2:
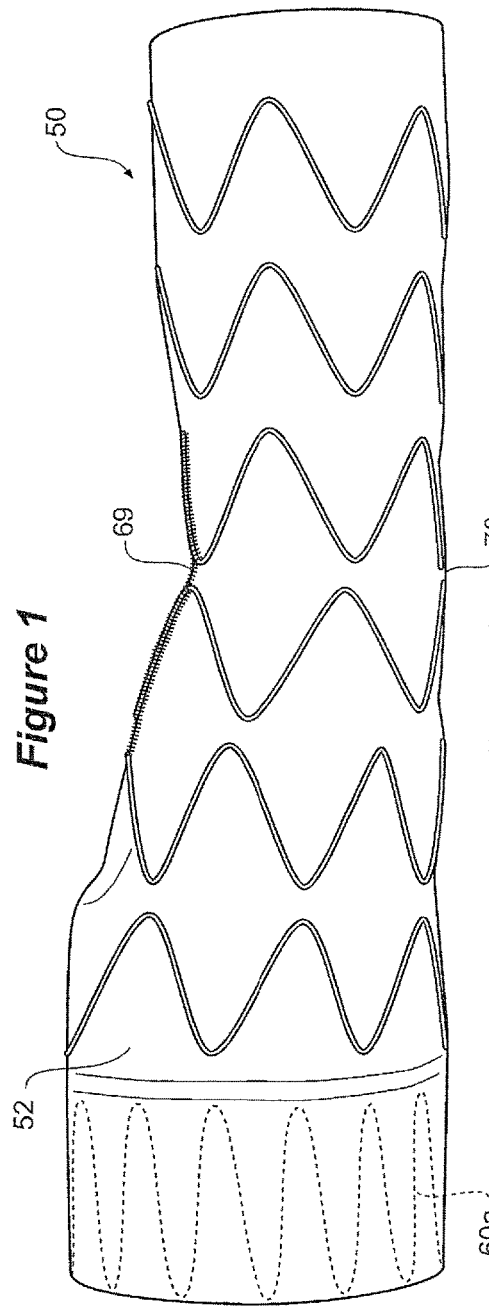
FIG. 2 shows a side view of the stent graft of FIG. 1.

Referring to FIG. 1 it can be seen that the proximal portion 54 comprises a tubular body of a biocompatible graft material and is supported by self expanding zig zag stents 60a and 60b. The stent 60a is internal to provide a smooth sealing surface to engage against the wall of the ascending aorta, and the stent 60b is external. The proximal portion may have a diameter from 35 to 50 mm.

The distal portion 58 is again formed from a tubular body of a biocompatible graft material and is supported by self expanding zig zag stents 82 and 84. The distal portion 58 can have a diameter in the range of from 30 to 40 mm.

The intermediate portion 56 is supported by self expanding zig zag stents 64 and 66 and is the region into which are placed the diamond shaped regions and the recess according to the present invention. The intermediate portion has a diameter in the range from 20 to 30 mm and had tapered portions at each end to connect with the proximal and distal portions respectively.

The stents 64, 66 and 68 comprise a plurality of struts and bends, the bends between the adjacent struts. In the embodiment shown, the struts are substantially longer than the bends, the bends having a relatively small radius. The stents are made from shape memory wire in the form of nitinol (metal alloy of nickel and titanium).

The intermediate portion 56 has a diameter at its proximal end 61 which is substantially the same as the diameter of the proximal portion 54 and a diameter at its distal end which is substantially the same as the diameter of the distal portion 58. The intermediate portion 56 has most, if not all of its taper between the diameter of the proximal portion and the diameter of the distal portion on the outside 72 of the curve of the stent graft.

As can be seen in FIG. 1 the intermediate portion 56 has two apertures or fenestrations 74 and 75 which open into respective recesses 76 and 77 within the step portion and graft tubes from the recesses extends proximally towards the proximal portion 54.

Adjacent stents 64 and 66 are positioned such that they define a diamond shape region 76a. The diamond shape arises from having a pair of distal bends 64b and 64d of stent 64 aligned with a pair of proximal bends 66b and 66d of stent 66 as is clearly shown in FIG. 1. A first pair of adjacent struts 64b' and 64c' of stent 64 and a second pair of adjacent struts 66b' and 66c' of the adjacent stent 66 together define a diamond shaped region 76a.

A recess 76 lies within the diamond shape region 76a. A fenestration 74 into the tubular body leads from recess 76 into a graft tube 78. The graft tube 78 extends within the tubular body towards a proximal end of the stent graft as is most clearly shown in the cross-sectional view of FIG. 5.

A third adjacent stent 68 has a pair of bends 68a and 68c adjacent to the second stent 66 such that a third pair of adjacent stents 68a' and 68b' define a second diamond shape region 77a. The second diamond shape region 77a shares a strut 66b' with the first diamond shape region 76a.

Figure 6:
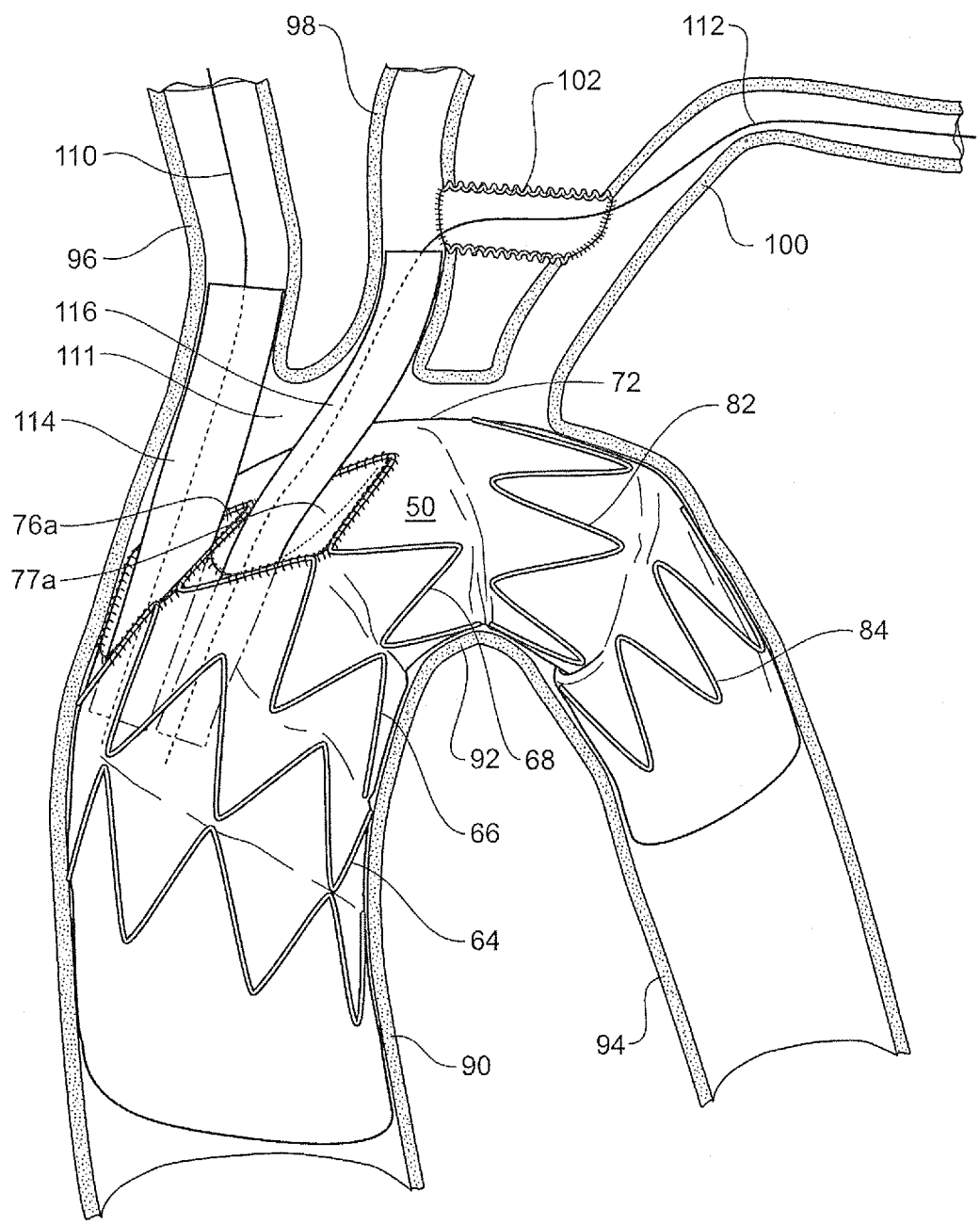
FIG. 6 shows a schematic view of the placement of a stent graft according to the present invention into the thoracic arch of a patient.

In this particular embodiment stent 64 has fourteen bends (seven distal bends and seven proximal bends) and stent 66 has twelve bends (six distal bends and six proximal bends). As a result of the differing number of bends and the alignment described above, distal bends of stent 64 are not aligned with proximal bends of stent 66 at the inside radius of the stent graft, the side of the stent graft without the diamond shaped regions, when it is placed in the arch as illustrated in FIG. 6. This assists in providing flexibility so as to facilitate the stent graft conforming to the anatomy of the thoracic arch as is shown in FIG. 6. In other embodiments different numbers of struts and bends may be used. In general, however, it is preferable for adjacent stents to have different numbers of struts and bends so that on the side of the stent graft without the fenestrations and recesses the bends do not coincide thereby allowing better flexibility.

The diamond shape regions and recesses 76a and 77a facilitate insertion of guide wires from the major branch arteries (such as the brachiocephalic and the left carotid artery) into the internal tubes 78 and 80 of the stent graft 50.

With the embodiment shown in FIGS. 1 to 6, the diamond shape regions 76a and 77a are adjacent each other and are separated by a strut 66b' of stent 66. With this arrangement, the corresponding fenestrations 74 and 75 are offset from each other so that one is slightly more ventral than the other with respect to the thoracic arch.

The recess 76 within the intermediate portion 56 opens at its proximal end into a tube 78 and the recess 77 opens at its proximal end into a tube 80. Each of the tubes may be of the same diameter or the uppermost of the tubes 78 may have a diameter which is greater than the diameter of the lower tube 80. The tubes 78 and 80 extend towards the proximal end 61 of the stent graft 50.

The proximal end of the tubes 78 and 80 are held open by reinforcing wires, or wire portions, 78a and 80a respectively, these wires arranged to form circles as is shown in the cross-sectional view of FIG. 5.

Figure 3:
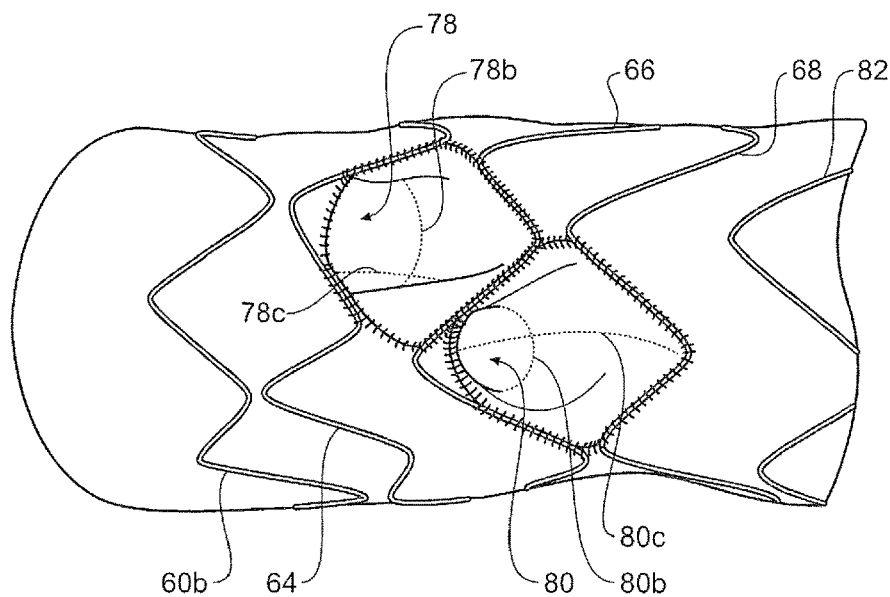
FIG. 3 is an isometric view looking in a slightly distal direction along the stent graft of FIG. 2.
Figure 4:
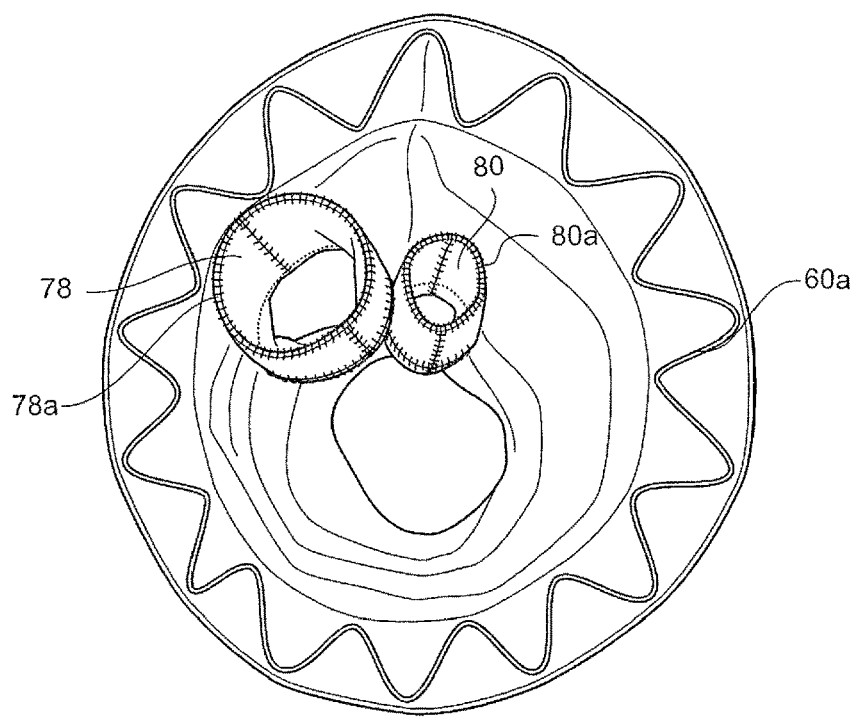
FIG. 4 shows a view from the proximal end of the stent graft shown in FIG. 1.

The tubes 78 and 80 also have reinforcing wires, or wire portions, 78b and 80b arranged to hold the respective distal ends of the tubes open as is more clearly shown in FIG. 3.

Extending from reinforcing wire 78a, past reinforcing wire 78b and to bend 66c is a longitudinal reinforcing wire, or wire portion 78c as is most clearly shown in FIG. 1. Similarly, extending from reinforcing wire 78a, past reinforcing wire 80a and to bend 68b is a longitudinal reinforcing wire, or wire portion 80c.

Each of the smaller internal tubes 78 and 80 can be reinforced with a helical shape memory wire reinforcement. Helical reinforcement for graft material is shown in U.S. patent application Ser. No. 12/261,860 entitled "Flexible Stent Graft" and the teachings therein are incorporated herein in their entirety.

FIG. 6 shows a schematic view of the placement of a stent graft according to one embodiment of the present invention into the thoracic arch of a patient.

The thoracic arch shown schematically comprises an ascending aorta 90 extending to the thoracic arch 92 and a descending aorta 94 from the thoracic arch. Substantially at the top of the thoracic arch but slightly to the ventral side of the arch the major vessels branch off the arch. The major vessels are the brachiocephalic artery 96, the left common carotid artery 98 and the left subclavian 100. In a preparatory operation an anastomosis 102 is provided between the common carotid artery 98 and the left subclavian 100. The anastomosis provides access between the common carotid artery 98 and the left subclavian artery 100 which enables endovascular access to the stent graft via brachial arteries in the left arm rather than endovascular access via the left carotid artery which may be more complex.

The stent graft 50 is deployed into the thoracic arch such that the intermediate portion 56 is just proximal of the junction of the aorta with the brachiocephalic artery 96. This means that there is defined between the intermediate portion 56, the upper wall of the thoracic arch and the distal portion 58 of the stent graft 50, an open region 111 so that circulation can be preserved to the major vessels through the internal tubes 78 and 80 and the recess 76 (see FIGS. 3 and 4) during the operation of deployment of the stent graft and subsequent placement of side branch grafts. The space also assists in enabling catheterisation of the internal tubes. A catheter 110 can be inserted to enter the larger of the tubes 78 to enable placement of a side branch stent graft 114 for the brachiocephalic artery 96 and a catheter 112 can be inserted to enter the smaller of the tubes 80 to enable placement of a side branch stent graft 116 for the common carotid artery 98 and the left subclavian artery 100. Subsequently a side branch stent graft can be deployed from the respective branch artery into one of the smaller tubes to provide blood flow into that branch artery.

Because the space 111 provides maintenance of circulation to the major vessels there may be circumstances where an operation can be carried out in stages.

In a preferred embodiment the larger of the internal tubes 78 has a diameter of from 8 to 12 mm and the smaller of the tubes has a diameter of from 8 to 10 mm.

The graft tubes extending into the main lumen can have a reinforcement in the form of a space frame. The components of the space frame can be an assembly of two ring and strut components. Each ring and strut component comprises a circular ring portion defining a plane of the circular ring portion and a strut extending at right angles to the plane of the circular ring portion from a periphery of the circular ring portion. Each of the two ring and strut components are formed from a single length of a rigid but resilient wire such as a nickel titanium alloy wire. At each end of each piece of wire a loop is formed to ensure that a sharp end which could puncture a vessel wall is not present. Once the components of the lightweight space frame are formed they have stitched to them portions of biocompatible graft material to form separately the tubular portion and the funnel portion and then these are joined together by stitching or the like.

Figure 7:
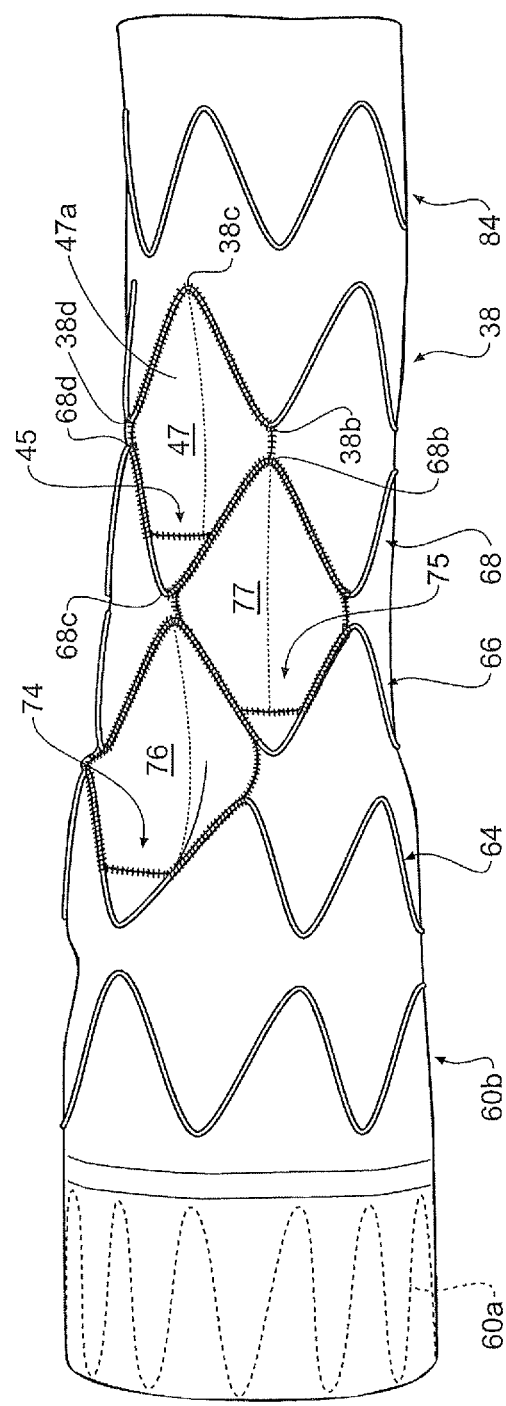
FIG. 7 shows a plan view of a second embodiment of a stent graft according to the present invention.

FIG. 7 shows an alternative embodiment. This embodiment is similar to that shown in FIGS. 1 to 6 but it includes a third diamond shaped region 47a with its corresponding recess 47 and fenestration 45. In other embodiments, not shown, there can be a single diamond shaped region, multiple diamond shaped regions aligned longitudinally or other layouts of the regions.

Many modifications and other embodiments of the invention will come to the mind of one skilled in the art having the benefit of the teachings presented in the foregoing descriptions and associated drawings. Therefore, it is understood that the invention is not to be limited to the specific embodiments disclosed, and that modifications and embodiments are intended to be included within the scope of the appended claims.

The invention claimed is:

1. A stent graft for placement in a vessel of a patient, the stent graft comprising:
    a tubular body of graft material, the tubular body having a proximal inflow end, a distal outflow end, a main lumen therethrough, and a sidewall from the proximal inflow end to the distal outflow end;
    a plurality of stents along the tubular body, including a first stent and second stent adjacent the first stent;
    a first recessed region in the graft material, the first recessed region defined by a recessed portion of the graft material of the tubular body that extends into the main lumen of the tubular body and a second recessed region defined by a second recessed portion of the graft material of the tubular body that extends into the main lumen of the tubular body, wherein the first recessed region and the second recessed region share a boundary;
    a first fenestration in the first recessed region of the graft material, a second fenestration in the second recessed region of the graft material, each of the first and second fenestrations opening into the tubular body, wherein the first and second fenestrations are both circumferentially and longitudinally offset from each other.

2. The stent graft of claim 1, further comprising:
    a first graft tube leading from the first fenestration into the main lumen toward the proximal inflow end and a second graft tube leading from the second fenestration into the main lumen toward the proximal inflow end.

3. The stent graft of claim 2, where in the first graft tube has a first diameter and the second graft has a second diameter greater than the first diameter.

4. The stent graft of claim 2, wherein the first and second graft tubes each comprise a space frame having first and second circular ring portions spaced apart axially and at least two struts extending between the first and second circular ring portions.

5. The stent graft of claim 2, wherein the first and second graft tubes each comprise a cylindrical portion, each cylindrical portion comprises an assembly of two individual ring and strut components, each ring and strut component comprising a circular ring portion defining a plane of the circular ring portion and a strut extending at right angles to the plane of the circular ring portion from a periphery of the circular ring portion.

6. The stent graft of claim 1, wherein each of the first and second recessed regions have a proximal end and at least one of the first and second fenestrations is disposed in the proximal end of its respective recessed region.

7. The stent graft of claim 6, wherein the first fenestration is disposed in the proximal end of the first recessed region and the second fenestration is disposed in the proximal end of the second recessed region.

8. The stent graft of claim 1, wherein the first and second recessed regions each comprise a diamond shape having first and second proximal sides meeting at a proximal apex and first and second distal sides meeting at a distal apex to form the diamond shape of each recessed region, wherein a distal side of the first recessed region shares the boundary with a proximal side of the second recessed region.

9. The stent graft of claim 8, wherein the first stent is a first zig zag stent and a second stent is a second zig zag stent directly adjacent the first zig zag stent, wherein the first and second zig zag stents define the diamond shape of the first recessed region.

10. The stent graft of claim 9, further comprising a third zig zag stent directly adjacent the second zig zag stent, wherein the second and third zig zag stents define the diamond shape of the second recessed region.

11. The stent graft of claim 10, wherein a single strut of the second zig zag stent defines a distal side of the first diamond shape and the proximal side of the second diamond shape.

12. The stent graft of claim 8, wherein proximally of the first diamond shape the tubular body has a first diameter, distally of the second diamond shape the tubular body has a second diameter, and in an intermediate region of the tubular body around the diamond shapes, the tubular body has a third diameter, the first diameter being greater than the second diameter and both the first and second diameter being greater than the third diameter.

13. The stent graft of claim 12, wherein the intermediate region tapers on only one side of the stent graft and the first and second recessed regions are disposed substantially in the taper of the intermediate region.

14. The stent graft of claim 1, wherein the first fenestration is proximal of the second fenestration.

15. A stent graft for placement in vessel of a patient, the stent graft comprising;
a tubular body of graft material, the tubular body defining a main lumen therethrough, the graft material defining a side wall, a plurality of zig zag stents along the tubular body, each of the stents comprising a plurality of struts and points or bends, each point or bend being disposed between a pair of adjacent struts;
a first shaped recess in the side wall of the graft material of the tubular body having a perimeter, the perimeter being formed at least in part by two adjacent struts of a first stent of the plurality of zig zag stents and two adjacent struts of a second adjacent stent of the plurality of zig zag stents;
a second shaped recess in the side wall of the graft material of the tubular body having a perimeter, the perimeter being formed at least in part by two adjacent struts of the second stent of the plurality of zig zag stents and two adjacent struts of a third adjacent stent of the plurality of zig zag stents, wherein the first shaped recess and the second shaped recess share a boundary at one of the two adjacent struts of the second stent and are longitudinally and circumferentially offset from one another;
the shaped recesses being defined by a respective recessed portion of the graft material that extends into the main lumen of the tubular body, the shaped recesses, having a proximal end;
a first fenestration in the first recessed portion of graft material, the first fenestration opening into the tubular body from the first shaped recess;
a second fenestration in the second recessed portion of graft material, the second fenestration opening into the tubular body from the second shaped recess
a first graft tube leading from the first fenestration into the main lumen and comprising a reinforcing assembly in the form of a space frame; and
a second graft tube leading from the second fenestration into the main lumen and comprising a reinforcing assembly in the form of a space frame.

16. The stent graft of claim 15, wherein the first graft tube extends from the proximal end of the first shaped recess and the second graft tube extends from the proximal end of the second shaped recess.

17. The stent graft of claim 16, wherein the stent graft comprises a proximal end and a distal end and each of the first and second graft tubes extend within the main lumen towards the proximal end of the stent graft.

18. The stent graft of claim 15, wherein each space frame comprises a cylindrical portion, each cylindrical portion comprising first and second circular ring portions spaced apart axially and at least two struts extending between the first and second circular ring portions and each graft tube being around the space frame.

19. The stent graft of claim 15, wherein the first graft tube has a greater diameter than the second graft tube.

20. The stent graft of claim 15, wherein each space frame comprises a cylindrical portion, each cylindrical portion comprises an assembly of two individual ring and strut components, each ring comprising a circular ring portion defining a plane of the circular ring portion and a strut extending at right angles to the plane of the circular ring portion from a periphery of the circular ring portion.

21. A stent graft for placement in a vessel of a patient, the stent graft having a proximal end and a distal end, the stent graft comprising:
a tubular body of graft material, the tubular body having a main lumen therethrough, the graft material defining an side wall, a plurality of discrete zig zag stents along the tubular body, each of the stents comprising a plurality of struts and bends, with each bend being disposed between a pair of adjacent struts;
at least a first stent of the plurality of zig zag stents, a second stent of the plurality of zig zag stents adjacent to the first stent, and a third stent of the plurality of zig zag stents adjacent to the second stent, the first stent having a pair of adjacent bends substantially aligned with a pair of adjacent pair of bends of the second stent and the second stent having a pair of adjacent bends substantially aligned with a pair of adjacent pair of bends of the third stent, whereby a pair of adjacent struts of the first stent and a pair of adjacent struts of the second stent together define a first diamond shaped region and a pair of adjacent struts of the second stent and the third stent together define a second diamond shaped region;
a first recess in the first diamond shaped region, the first recess being defined by a first recessed portion of the side wall of the graft material that extends into the main lumen of the tubular body, the first recess having a proximal end;
a second recess in the second diamond shaped region longitudinally and circumferentially offset from the first recess, the second recess being defined by a second recessed portion of the side wall of the graft material that extends into the main lumen of the tubular body, the second recess having a proximal end;
a first fenestration in the first recessed portion of graft material, the first fenestration opening into the tubular body from the first recess in the first diamond shaped region;
a second fenestration in the second recessed portion of graft material, the second fenestration opening into the tubular body from the second recess in the second diamond shaped region;
a first graft tube leading from the first fenestration into the main lumen, the first fenestration and the first graft tube extending from the proximal end of the first recess towards the proximal end of the stent graft; and a second graft tube leading from the second fenestration into the main lumen, the second fenestration and the second graft tube extending from the proximal end of the second recess towards the proximal end of the stent graft.

* * * * *

UNITED STATES PATENT AND TRADEMARK OFFICE
CERTIFICATE OF CORRECTION

PATENT NO. : 10,231,822 B2  
APPLICATION NO. : 15/593715  
DATED : March 19, 2019  
INVENTOR(S) : David Ernest Hartley Page 1 of 1

It is certified that error appears in the above-identified patent and that said Letters Patent is hereby corrected as shown below:

In the Claims

In Column 8, Claim 3, Line 36, after "the second graft" insert --tube--.

In Column 9, Claim 11, Line 9, after "zig zag stent defines" replace "a" with --the--.

Signed and Sealed this
Eighteenth Day of June, 2019

Andrei Iancu
*Director of the United States Patent and Trademark Office*